United States Patent [19]
Faughn

[11] Patent Number: 5,738,143
[45] Date of Patent: Apr. 14, 1998

[54] BUTTERFLY ACTUATED QUICK COUPLING CONNECTOR VALVE

[75] Inventor: Jim A. Faughn, Bel Air, Md.

[73] Assignee: The United States of America as represented by the Secretary of the Army, Washington, D.C.

[21] Appl. No.: 700,558

[22] Filed: Aug. 8, 1996

[51] Int. Cl.$^6$ ............................................. F16L 29/00
[52] U.S. Cl. ............................. 137/614.03; 251/149.2
[58] Field of Search ................... 137/614.02, 614.03; 251/149.2

[56] References Cited

U.S. PATENT DOCUMENTS

| | | | |
|---|---|---|---|
| 2,300,483 | 11/1942 | Berger et al. | 251/149.2 X |
| 3,028,179 | 4/1962 | Abramoska . | |
| 3,077,330 | 2/1963 | Lamphear | 251/149.2 X |
| 3,191,972 | 6/1965 | Collar . | |
| 3,478,302 | 11/1969 | Chirumbolo . | |
| 3,625,251 | 12/1971 | Nelson . | |
| 4,625,746 | 12/1986 | Calvin et al. | 251/149.2 X |
| 5,009,252 | 4/1991 | Faughn . | |
| 5,090,448 | 2/1992 | Truchet | 251/149.2 X |
| 5,174,373 | 12/1992 | Shinmura . | |
| 5,187,316 | 2/1993 | Hasler et al. . | |
| 5,257,653 | 11/1993 | Nimberger . | |
| 5,351,708 | 10/1994 | Donato et al. | 137/614.02 X |

Primary Examiner—Kevin Lee
Attorney, Agent, or Firm—Freda L. Krosnick; Paul S. Clohan

[57] ABSTRACT

A butterfly actuated quick coupling connector valve includes a pair of mating connectors, each having a self-closing, butterfly valve arranged and adapted to align with the self-closing, butterfly valve of the other connector when the two connectors are coupled together, such that the two valves will be then open for unrestricted passage of air therethrough. Each connector has a coupling mechanism for releasably coupling the two connectors together to cause interference between them. Each of the valves is attached to a plunger, and a compression spring is associated and aligned therewith, in a valve housing having an axis of symmetry within the associated connector. Each plunger is retained and slidable axially within the housing against the force exerted by the associated compression spring, the latter normally urging the valve body against an end wall of the housing to block an opening therein. The plunger has a rotatable shaft attached to it with a butterfly valve mounted to its centerline surface. This assembly moves forward and rearward with the plunger and rotates 90 degrees at the rearward most portion of its travel. This rotation allows the passage of air, gases, and fluids to flow without restriction through the entire connector valve. Thus, air and other substances are allowed to pass from one end to the other of the coupled connectors by virtue of the respective butterfly valves having been unseated from their associated end walls and rotated by means of springs and/or a cam path.

16 Claims, 9 Drawing Sheets

BUTTERFLY ACTUATED QUICK COUPLING CONNECTOR VALVE

RIGHTS OF THE GOVERNMENT

The invention described herein may be manufactured, used, and licensed by or for the United States Government for governmental purposes without the payment to me of any royalty thereon.

BACKGROUND OF THE INVENTION

1. Field of the Invention

The present invention relates generally to air distribution systems, and more particularly to an air distribution connector valve for rapidly and positively connecting and disconnecting a life support system to and from a main supply of air.

2. Discussion of Related Art

Various life support systems have been proposed in the past to provide air flow or distribution to one or more human subjects under conditions in which a breathable atmosphere is otherwise unavailable. Exemplary of such conditions are toxic fumes and particles encountered by soldiers operating in nuclear, biological, and chemical (NBC) contaminated battlefields, workers involved in the cleanup of toxic waste dumps, cleanup crews removing asbestos, lead paint abatement, bio-hazard spills, painting, sand blasting, welding, etc.

Some life support systems comprise a breathing apparatus employing a filter to remove the noxious or toxic elements from the air. In general, however, most life support systems are characterized by a self-contained source or supply of breathable air connected to a mask or hood that is placed over the head, or simply the eyes, nose, and mouth of the user. In some instances, the system is intended for a single user, while in many others a single air supply is available for use by several persons.

Most of the prior art valves used to control air distribution in life support systems suffer certain disadvantages, principal among which are a lack of free flow of air through the open valve(s), difficulty of manually opening and closing the valve by the user, particularly in emergency situations, lack of a positive indication to the user that the valve is fully open or closed, and inadequate coupling mechanisms for the valves. Also, current valves are not designed for easy decontamination, since they have connection devices, grooves, channels, ball bearings, and other crevices and configurations which can harbor contamination and which are virtually impossible to decontaminate with field expedient measures.

U.S. Pat. No. 5,009,252 (incorporated by reference herein) to Faughn discloses an air distribution connector valve which addresses many of these disadvantages. This prior art valve includes a positive locking connector which provides visual, audible, and tactile feedback when fully engaged, and a poppet valve mechanism which produces little restriction to the air flowing through the connector valve. However, experimentation with this valve has shown that restriction of air flow by the poppet valve is still more than ideal and that recessed surfaces located at the connection point between each valve half make it difficult to decontaminate the valve.

SUMMARY OF THE INVENTION

Accordingly, it is a principle object of the present invention to provide a connector valve which allows full, unrestricted, near-laminar air flow through the valve.

It is another object of the invention to provide a connector valve which is easy to decontaminate.

A connector valve according to the present invention comprises two mating components, each of which contains a self-closing, butterfly valve. When the two mating components are coupled together both butterfly valves open to allow air to pass with little or no restrictions through the connector valve. The connector valve incorporates a positive locking connector to facilitate the coupling and locking of the two mating components.

In particular, a connector valve according to the invention includes first and second mating connectors, each of which has a self-closing, butterfly valve in a valve housing, with each butterfly valve being arranged and adapted to open when the two connectors are mated together, whereby the two valves form a passageway for unrestricted flow of air therethrough. Each connector also has an engagement mechanism for separably coupling the two connectors together.

Each of the butterfly valves comprises a thin disk attached to a rotatable shaft and is associated with an operating plunger, the valve and plunger being retained and slidable axially within the valve housing. When uncoupled, each of the operating plungers project axially from the end of the valve housing and the butterfly valve of each connector is pushed by a force exerted by an associated compression spring against an end wall of the housing having an orifice, whereby the disk is seated against the end wall and blocks the orifice.

Each plunger has an angled end surface arranged and adapted to confront, align, and abut against the opposing angled end surface of the other plunger. As the two connectors are brought together by their respective engagement mechanisms, the plungers push against each other, thereby causing each butterfly valve to slide within the housing away from the orifice, with the shaft keeping the disk normal to the valve housing's centerline. When the two connectors are fully coupled together, each shaft rotates the disk 90 degrees to form an air distribution passageway. This process is reversed when the connectors are uncoupled such that each disk is rotated back 90 degrees by its shaft and is then reseated against the orifice of the valve housing.

The present invention has a number of advantages over prior art air distribution valve mechanisms. The low restriction of air flow provided by the present invention decreases demand on an air distribution system's requirements to overcome head loss, i.e. pressure restrictions, thereby enabling the use of a smaller air supply/life support system requiring less energy, size, and space. The present invention is readily decontaminated because its connection feature is independent of the valve feature, and the valve feature has smooth, flat exposed surfaces that are extremely easy to decontaminate with field decontamination procedures. In addition, the connector valve of the present invention provides additional safety in that no areas are exposed which could hold or harbor contamination, which could bleed out later into the air stream of the user.

BRIEF DESCRIPTION OF THE DRAWINGS

The above and still further objects, features, and attendant advantages of the invention will be better understood and appreciated from a consideration of the following detailed description of a presently preferred embodiment, taken in conjunction with the accompanying drawings in which:

FIGS. 10A–10I show details of the arrangement of FIG. 9B.

FIGS. 11A–C illustrate the movement and rotation of the shaft shown in FIGS. 7 and 8 during coupling and uncoupling of the connectors in two alternative embodiments of the invention.

DETAILED DESCRIPTION OF THE PREFERRED EMBODIMENTS

Figure 1:
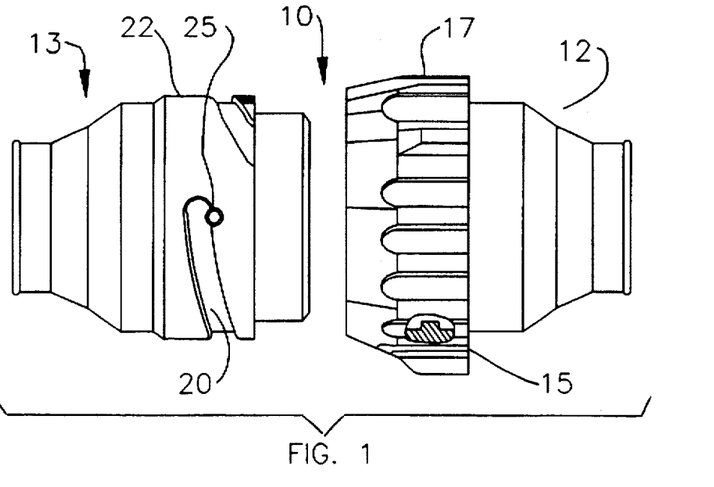
FIG. 1 is a side view, partly in section, of the male and female connector segments of an embodiment of the invention, in uncoupled, or valve closed configuration.
Figure 2:
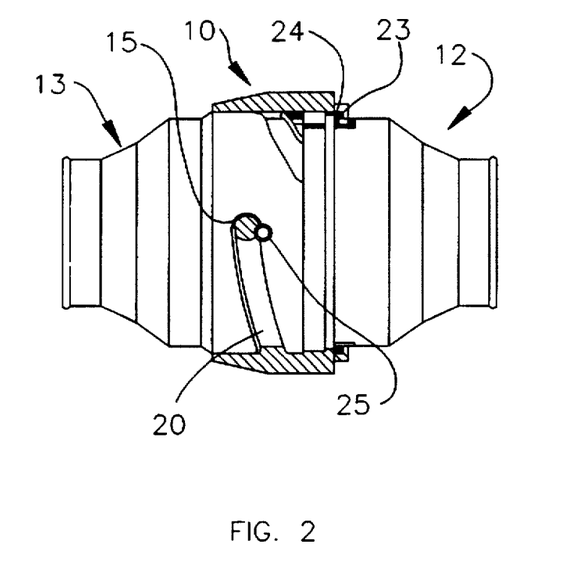
FIG. 2 is a side view, partly in section, showing the connector segments of FIG. 1 in coupled, or valve opened, configuration.
Figure 5:
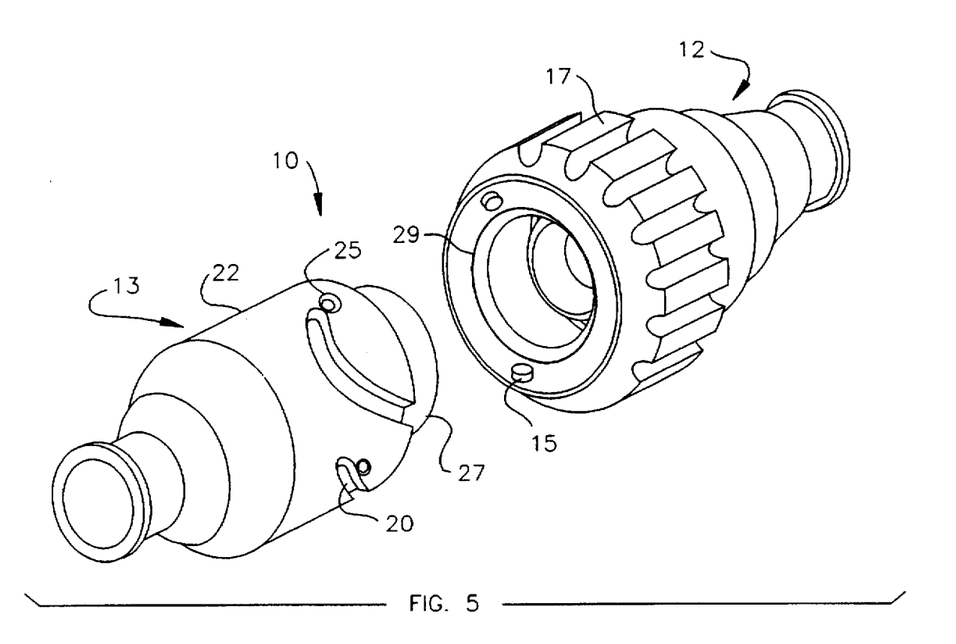
FIG. 5 is a perspective view of the two connector segments in the uncoupled state.

Referring to FIGS. 1, 2, and 5, an embodiment of a butterfly actuated quick coupling connector valve (BAQCCV) 10 according to the invention includes female and male mating connectors 12 and 13. Both the female connector 12 and the male connector 13 include a "CIR" Series coupling of a type widely used for electrical multi-pin connectors, manufactured by the Veam Division of Litton Systems, Inc. of Watertown, Conn. Such connectors are used in military, commercial, medical, geophysical, aerospace, ground support, and other applications, and feature a positive lock, quick-connect/disconnect coupling, and a dynamic seal mechanism requiring only a quarter of a turn for full mating or release. Full coupling is indicated by audible, visual, and tactile sensing. High shock and vibration resistance to 50 g's are attained without the use of lockwires or other secondary retaining mechanisms. The connector design avoids the use of coupling threads, which could gall or bind with wear or contamination. A stainless steel lock ring is provided at the high point of the bayonet ramp of the connector as a wear-free detent for extended coupling life. Said U.S. Pat. No. 5,009,252 describes the "CIR" connector in greater detail.

The coupling mechanism of the connectors is configured as follows. Female connector 12 has three equally spaced lugs or teeth 15 disposed internally on and integral with a captive, rotatable ring 17. A portion of the female connector 12 is shown in section in FIG. 1 to illustrate more clearly the location of one of the lugs 15 on the inner surface offing 17. Male connector 13 has three equally spaced helical grooves 20 in a circumferential collar 22. The grooves 20 are arranged and adapted to receive and accept the lugs 15 of the female connector 12, so that after the connectors 12 and 13 are placed in confronting relationship and the end 22 of male connector 13 is inserted with proper alignment into the rotatable ring 17, the lugs 15 are engaged in the grooves 20.

As shown in FIG. 2, the connectors 12 and 13 are fully coupled by rotating the ring 17 in a clockwise direction (as viewed from the right side of the Figure), thereby forcing the lugs 15 along the helical paths of grooves 20 until each of the lugs 15 is positioned over-center on a respective pin 25 near the end of the associated groove 20 and finally resides seated against the end of the groove 20. The lugs 15 are maintained in that position under the force of rearward axial tension placed on the lugs 15 by a wave spring or wave washer 23 which is seated, together with an associated flat washer 24, between confronting flanges of ring 17 and the connector 13 body. In this manner, the male and female connectors 12 and 13 are maintained in a positive locking connection. The user is thereby provided with visual, audible, and tactile evidence that the two connectors are fully coupled together.

When connectors 12 and 13 are to be separated (uncoupled), the user simply grasps the rotatable ring 17 with one hand, and exerts a force toward the male connector 13 while twisting the ring 17 in the counter-clockwise direction (as viewed in the same direction as before), to overcome the tension on locking pins 25 and return the lugs 15 along the grooves 20 to the exit points. Connector 12 is then merely pulled from connector 13 to fully uncouple the two. Thus, the connectors 12 and 13 are readily coupled and uncoupled using only one hand. This assumes, of course, that one or both of the connector bodies are held to preclude rotation, but to allow sufficient axial movement for manual separation and recoupling.

Figure 3:
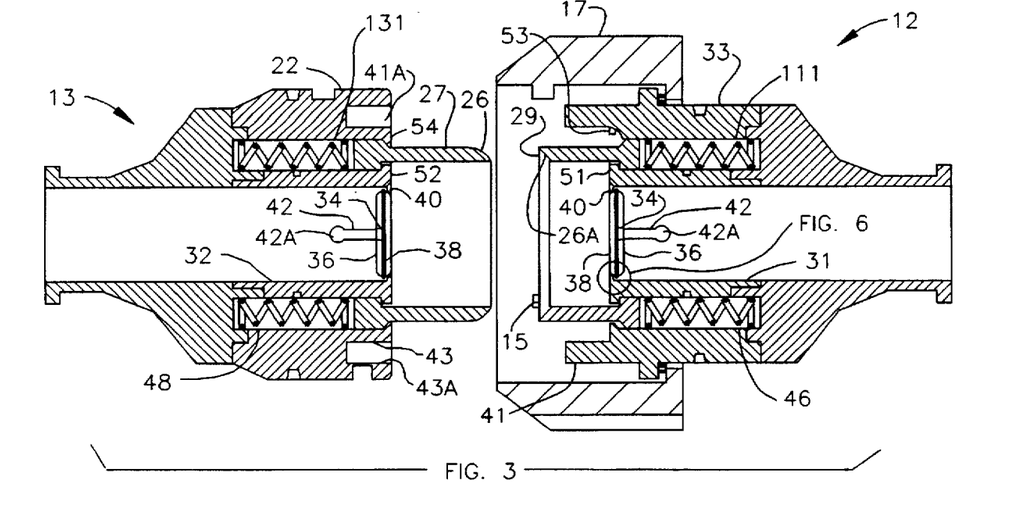
FIG. 3 is a side view corresponding to that of FIG. 1, in full section to show the internal components of the valving mechanism when the connectors are in the uncoupled configuration.
Figure 4:
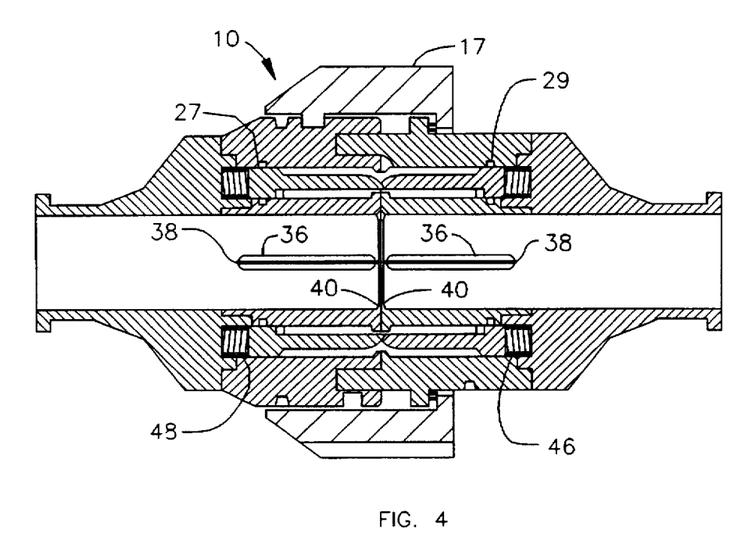
FIG. 4 is a section view of the internal components of the valving mechanism when the connectors are coupled as in FIG. 2.
Figure 6A:
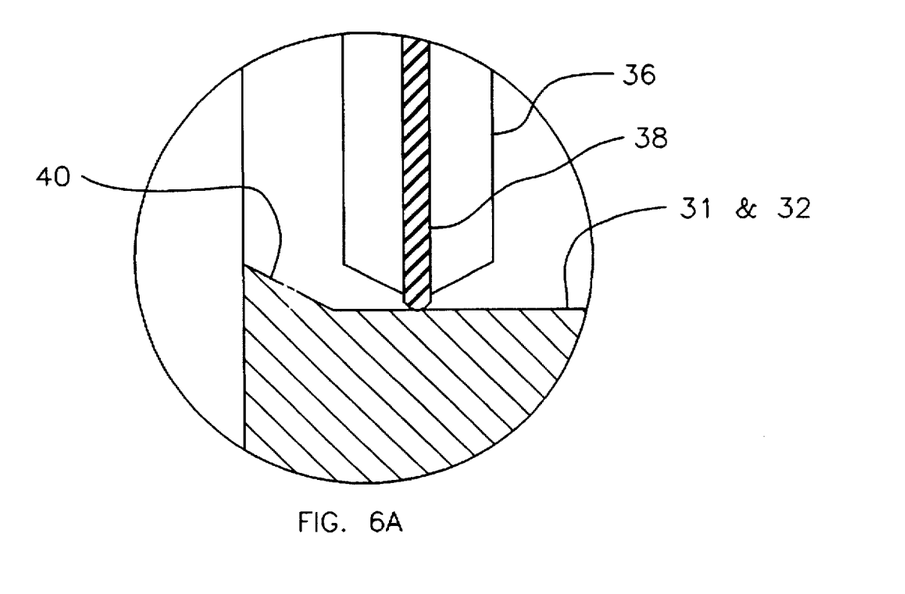
FIGS. 6A and 6B are partial blown-up views of FIG. 3, depicting how the butterfly valve becomes seated against the opening of the valve housing during uncoupling of the connectors.
Figure 6B:
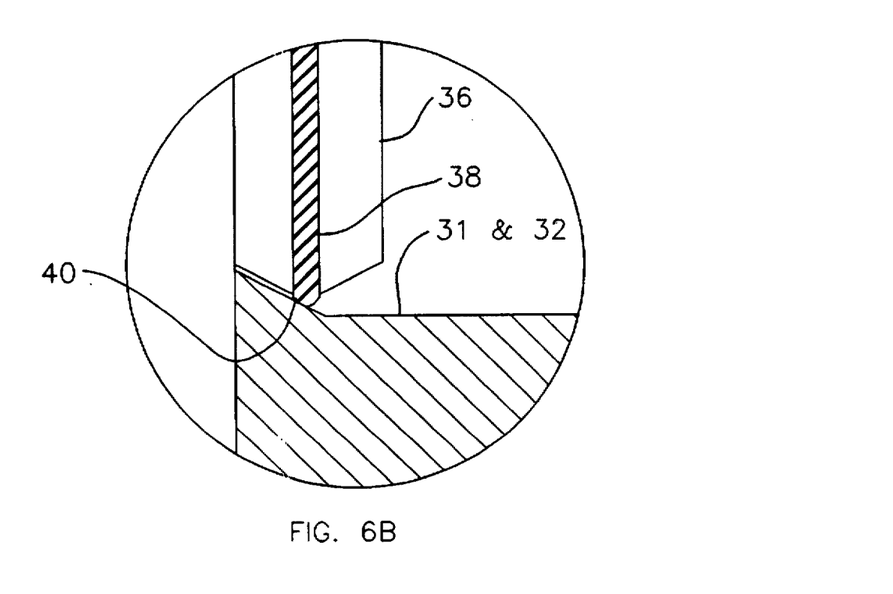

Referring now to FIGS. 3, 4, and 6, the illustrated embodiment includes first and second sliding operating plunger mechanisms 27 and 29, each having a substantially cylindrical body with a hollow center which is positioned on the axis of the inner valve housings 32 and 31, respectively. The internal diameter of plunger 27 slides in a cylindrical space 13 1 defined by the outside diameter of inner valve housing 32, and the inside diameter of circumferential collar 22. The internal diameter of plunger 29 slides in a cylindrical space defined by the outside diameter of valve housing 31, and the inside diameter of outer valve housing 33. Plungers 27 and 29 have opposing angled end portions 26 and 26a, respectively, adapted to confront, align, and abut against each other. In a preferred embodiment, one or both of angled end portions 26 and 26a are provided with at least one small, radially oriented depression (not shown) running from the internal diameter to the exterior diameter of angled ends 26 and/or 26A. Preferably, the depression is smooth and has generous curves to allow for ease of decontamination. Plunger 27 is retained by two projections normal to the axis of inner valve housing 32 which forms lips 52 and 54 at the end of inner valve housing 32 and circumferential collar 22, respectively. Plunger 29 is retained by two projections normal to the axis of inner valve housing 31 which forms lips 51 and 53 at the end of inner valve housing 31 and outer valve housing 33, respectively.

Figure 7:
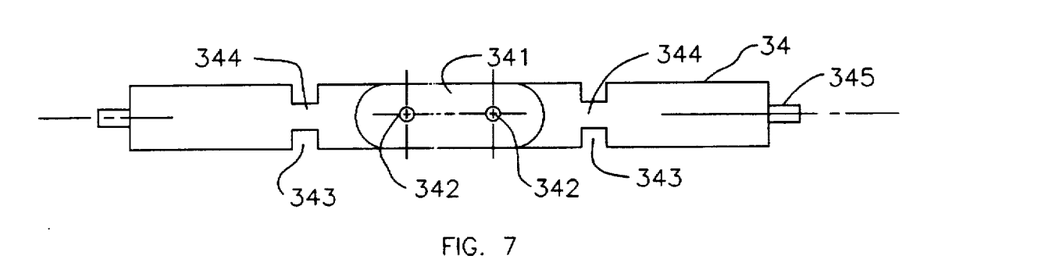
FIGS. 7 and 8 illustrate the rotating shaft for the valve.
Figure 8:
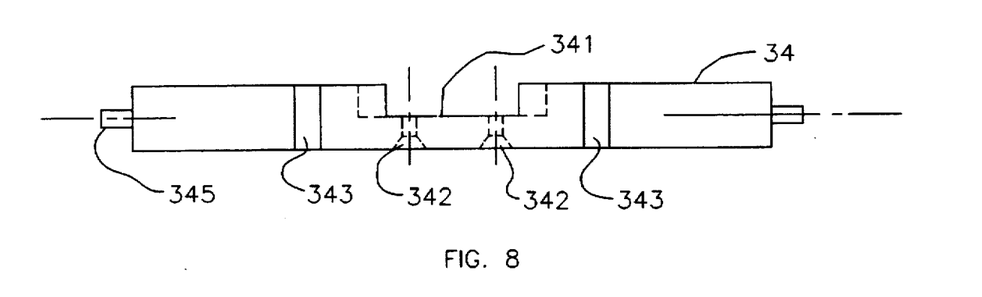
Figure 9A:
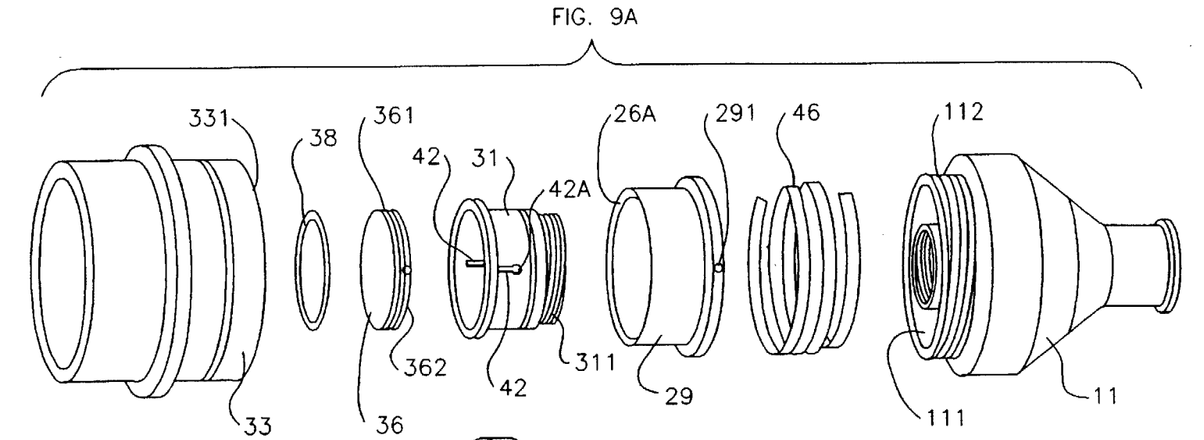
FIGS. 9A and 9B are an exploded view of a valve half.
Figure 9B:
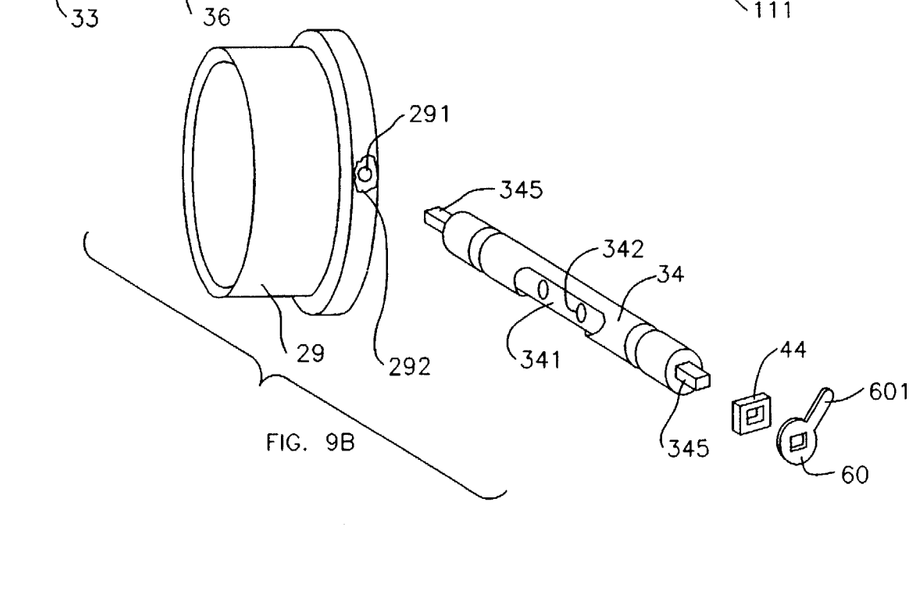

Each of the plungers 27 and 29 has the following features, although for brevity, the features are described only as to plunger 29. The plunger holds a rotatable shaft 34 which mounts to the plunger through two through holes 291 normal to the axis of the plunger as shown in FIGS. 9A and 9B. As shown in FIGS. 7 and 8, each shaft 34 has a flat surface 341 which forms a mounting surface to which a butterfly valve member 36 is attached. Butterfly valve 36 is a thin cylindrical disk which has a groove 361 cut into its outermost surface to attach a sealing mechanism or O-ring 38, which seals with the internal diameter of inner valve housing 31 or 32, and seals with angled flanges 40 located at the end of inner valve housing 31 or 32. Each of the inner valve housings 31 and 32 has two opposing rectangular slots 42 cut through the housing wall; the rotatable shaft 34 has corresponding notches 343 on its shaft which slidably engage with the two slots 42. The plunger 29 has two biasing elements 44, which may be elastomeric bushings or coil springs as shown in FIGS. 10A–I. Biasing elements 44 mount into pockets 292 surrounding the through-holes 291 on the outer surface of the plunger 29. Elements 44 are anchored to the plunger 29 and attached to the rotatable shall 34 as described below and shown in FIGS. 9A, B and 10A–I. They operate to apply rotational force on the shaft 34 to make it rotate 90 degrees once free of the two slots 42. Movements of the plungers 27 and 29 are opposed by compression springs 48 and 46, respectively, which tend to push the plungers 27 and 29 forward toward the end of the valve housing at all times (see FIG. 3); but when connectors 12 and 13 are manually coupled, they compress as plungers 27 and 29 interact (see FIG. 4).

The connectors 12 and 13 are nearly identical in their internal construction and operation. The plungers 29 and 27 abut each other and push against each other as connectors 12 and 13 are brought together. The pushing of plungers 29 and 27 against each other is the mechanism responsible for sliding the butterfly valves 36 rearward. As connectors 12 and 13 are brought together, an axially projecting cylindrical ring 41 on female connector 12 mates into a corresponding groove 41A on male connector 13. When the ring 41 enters groove 41A, it may contact optional O-rings 43 and 43A which seal against the inside diameter and outside diameter, respectively, of projecting ring 41. Optional O-rings 43 and 43A cause an interference with ring 41 and form a liquid tight seal useful in fluid applications of the valve.

Assembly of the BAQCCV

For ease of description and brevity, assembly of only one half of the valve, i.e., connector 12, will be discussed; the other half is assembled in a similar fashion.

As shown in FIGS. 9A and 9B, butterfly valve 36 containing O-ring 38 is inserted into inner valve housing 31 and then pushed toward the end of slots 42 until edge 362 of the valve 36 just reaches the beginning of enlarged end portion 42A. The threaded end 311 of inner valve housing 31 is then inserted into the angled end 26A of plunger 29 and the valve housing is pushed into plunger 29 until the two opposing end portions 42A are aligned with the two opposing through holes 291 of plunger 29. Next, one drive end 345 of the rotatable shaft 34 is inserted into plunger 29 and inner valve housing 31 through one of the opposing pairs of aligned through holes 291 and enlarged end portions 42A and the rotatable shaft 34 is pushed until the aforesaid inserted drive end 345 exits the plunger 29 and inner valve housing 31 through the other pair of aligned through holes 291 and end portions 42A.

Butterfly valve 36 is then pushed towards the rotatable shaft until it rests on the flat surface 341 of the rotatable shaft 34. The butterfly valve 36 is secured in locked and intimate contact with the rotational shaft 34 by inserting two screws (not shown) through the two screw holes 342 of rotatable shaft 34 and turning the screws until they are threaded into the butterfly valve 36.

Figure 10A:
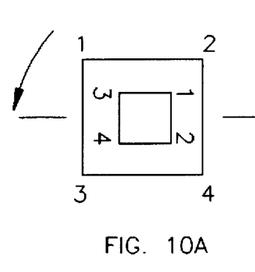
Figure 10B:
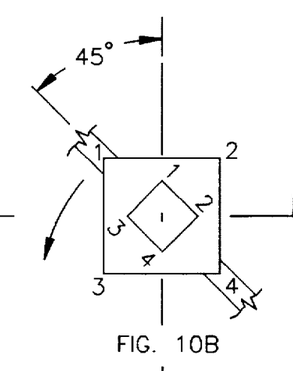
Figure 10C:
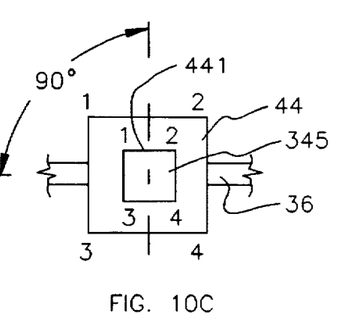
Figures 10D, 10E:
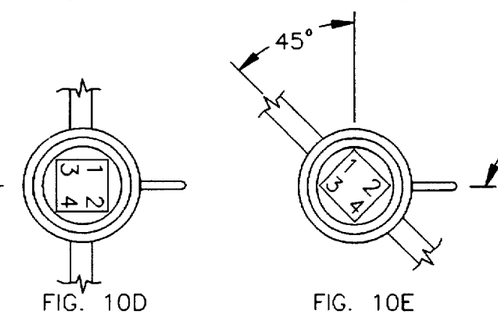
Figure 10F:
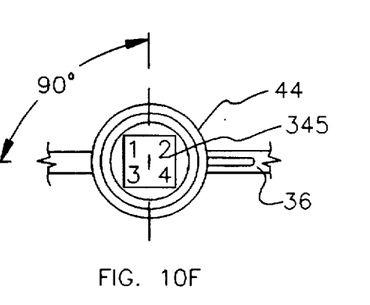

Next, the rotatable shaft 34 is rotated so that the butterfly valve 36 is parallel to the axis of inner valve housing 31 and plunger 29. A biasing element 44 is inserted into each of the two pockets 292 of plunger 29, aligning each of the drive ends 345 of the rotatable shaft 34 with the mating drive mechanism 441 of biasing elements 44 as shown in FIG. 10C. If the biasing element 44 is a coil spring as shown in FIGS. 10D–F, one end of the spring (not shown) is secured to the pocket 292 of plunger 29 and the spring's opposing end (not shown) is secured to the drive end 345. The biasing elements 44 are secured in place by pressing/screwing a tinnerman/timing nut 60 onto each drive end 345 until movement of arm 601 of the nut 60 is contained by pocket 294.

The compression spring 46 is then placed into a circular groove 111 located in the threaded end 112 of main body housing 11. Threaded end 112 has internal threads and external threads to receive the exterior threads on end 311 of inner valve housing 31 and the internal threads on end 331 of outer valve housing 33, respectively. Assembly of connector 12 is completed by screwing inner valve housing 31 into main body housing 11 followed by screwing outer valve housing 33 onto the main body housing 11. After the valve half is assembled, the compression spring 46 will push the plunger 29, rotatable shaft 34, and butterfly valve 36 forward into the closed position in which the butterfly valve 36 is normal to the axis of the inner valve housing 31 and flush against the beveled interior lip 40 of inner valve housing 31. The forward movement of the rotatable shaft applies a rotational torque to biasing elements 44 as described below and shown in FIGS. 10A–F.

Operation of the BAQCCV

Figure 11A:
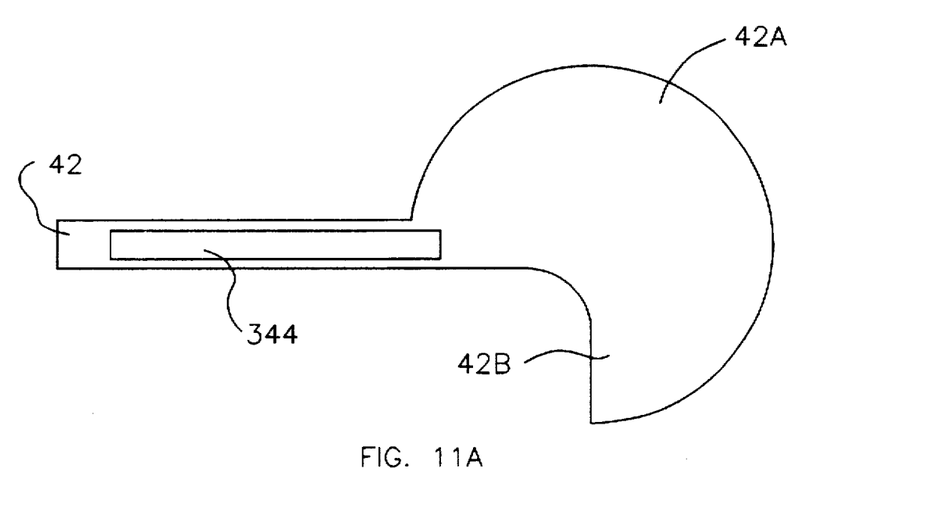

In a preferred use of the connector valve, male connector 13 is attached to a supply of clean air or fluid, and thus may be referred to as the supply side connector, while female connector 12 is attached to the entity receiving the supplied air or liquid, and is referred to as the receiving side connector. As the two valve halves are brought together, angled complementary surfaces 26 and 26A on operating plungers 27 and 29, respectively, align, orient, and abut with each other, forming a temporary joined configuration. Because compression spring 46 is more resistant than compression spring 48, supply side plunger 27 begins to move rearward against the opposing force of compression spring 48 before the receiving side plunger 29 begins to move. Plunger 27 begins to slide the rotatable shaft 34 and the butterfly valve 36 rearward along the two rectangular slots 42 in the wall of valve housing 32. Butterfly valve 36 cannot rotate because the longer dimension of rectangular shaft portion 344 left by notches 343 of the rotatable shaft 34 is greater than the shorter dimension of slots 42 (see FIG. 11A); thus the shaft 34 and attached butterfly valve 36 are permitted to slide axially, yet are not permitted to rotate.

Figure 11B:
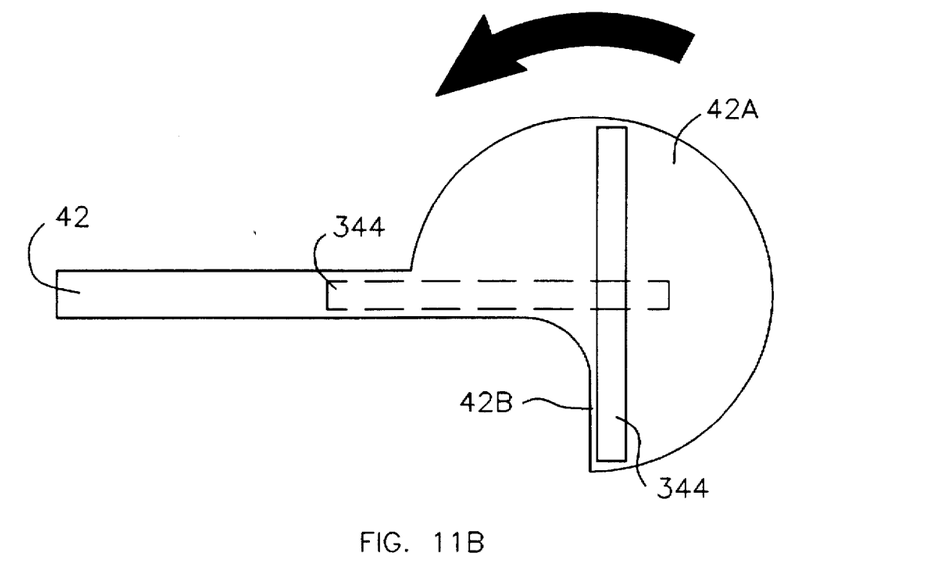

As shown in FIG. 11B, plunger 27 continues to move rearward until the shaft 34 reaches the enlarged end portion 42A of slots 42, at which time biasing elements 44 mounted in plunger 27 and connected to shaft 34 with the Tinnerman/ timing nuts 60 rotate both the shaft 34 and the butterfly valve 36 ninety degrees; this rotation is possible because the dimensions of end portion 42A are larger than the longer dimension of shaft portion 344. This rotation is achieved by placing bias elements 44 under a fun load rotational torque in the position shown in FIG. 3 when valve 36 is fully closed. When the rotatable shaft 34 reaches the end portions 42A of slots 42, the rotational torque stored by the bias elements 44 begins to rotate shaft 34 and the butterfly valve 36 to the open position.

Once valve 36 has been rotated 90 degrees, it is fully opened and the Tinnerman/timing nut 60 prevents further rotation of valve 36, i.e., beyond 90 degrees, because the timing arm 601 of the Tinnerman nut 60 abuts against a wall of cutout 294 (see FIGS. 9 and 10G–I), thereby securing the valve 36 in a position parallel to the axis of the valve housing and minimizing the restriction of air flow through the valve. Alternatively, the Tinnerman/timing nut 60 may be eliminated by providing enlarged end portion 42A with surface 42C as shown in FIG. 11C, wherein the surface 42B & C prevents rotation of shaft 34 beyond 90 degrees.

Figure 11C:
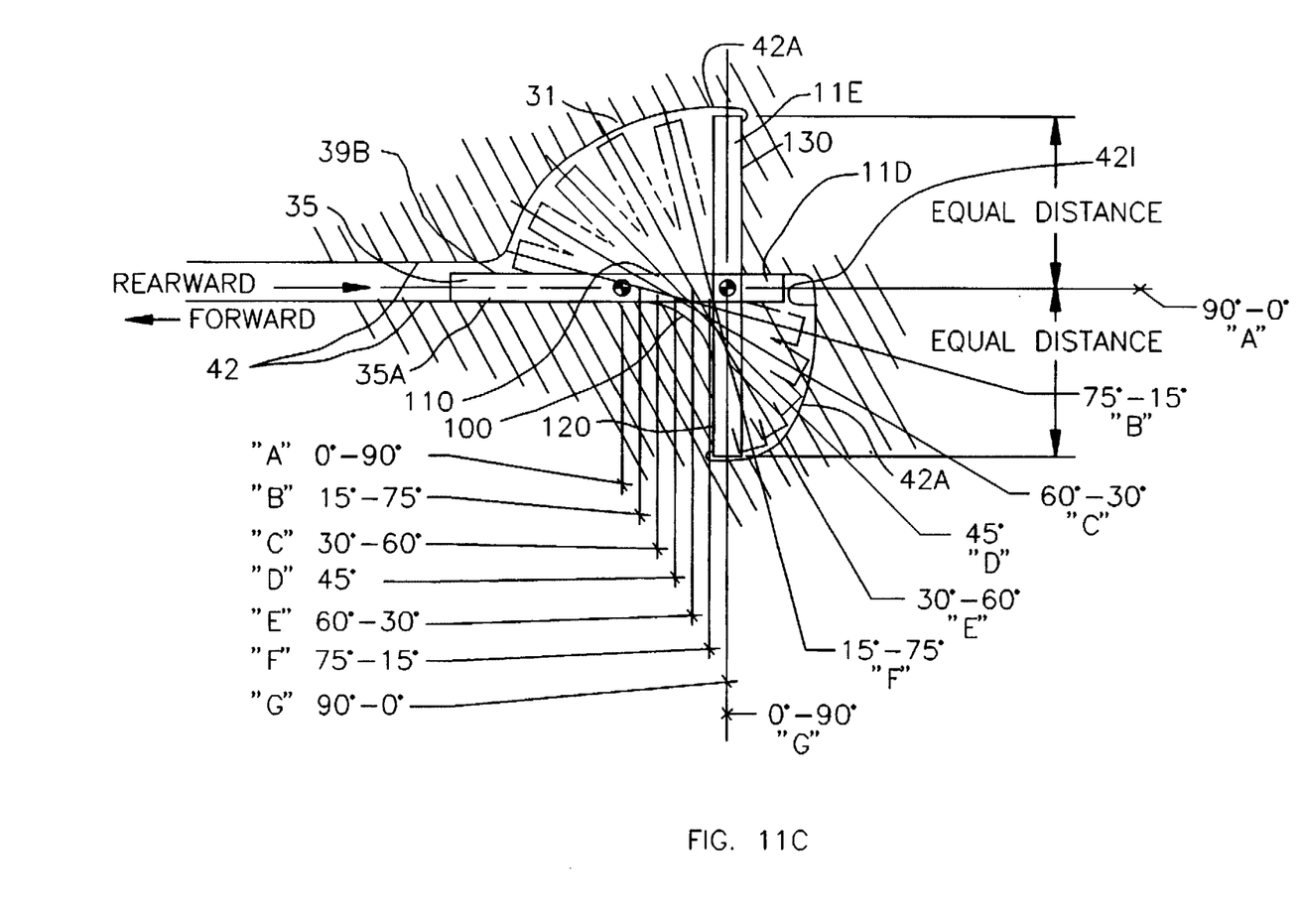

In the position shown in FIGS. 11B & 11C, butterfly valve 36 of supply side connector 13 is parallel with the longitudinal axis of the valve housing 32 and open, permitting unrestricted flow of the gas through the internal diameter of valve housing 32. This flow is near laminar because of the minimal restriction and turbulence generated by the thin butterfly valve 36 and rotatable shaft 34. When the supply side valve 36 is opened, clean air flows toward the valve 36 in receiving side connector 12 and exits the abutting plungers 27 and 29 through the depressions (not shown) on angled end 26A of plunger 29 and/or on angle end 26 of plunger 27, thereby purging the inner diameters of plungers 27 and 29 of any contamination as the receiving side plunger 29 begins to move rearward. In addition, the exiting gas cleans the area between the plunger 29 and projection ring 41 until projection ring 41 has mated with cylindrical groove 41A; at this position the connectors 12 and 13 form an airtight configuration, thereby ending the purging effect. Alternatively, the gas may exit the abutting plungers 27 and 29 by providing at least one through hole in the wall of receiving side plunger 29 and located adjacent to end 26A.

This purging feature may be eliminated in an alternative embodiment by providing equal force compression springs 48 and 46 which allow the two plungers 27 and 29 to move simultaneously and hence the two valves 36 to open simultaneously.

When plunger 27 reaches end portions 42A and valve 36 begins to open, plunger 29 begins to move rearward as further manual force is applied to the "CIR" connector. Valve 36 of plunger 29 is opened by an operation similar to that described above for plunger 27.

As connectors 12 and 13 are brought together, the circular projection ring 41 also aligns with the mating cylindrical groove 41A and begins to enter groove 41A. As the ring 41 enters groove 41A, its inside and outside diameters may contact optional O-rings 43 and 43A, respectively; this causes a liquid tight seal to be formed between connectors 12 and 13 for use with liquids. The interference and mating of projection ring 41 and groove 41A provide great strength to the valve assembly 10, especially against side and/or radial loading. When both plungers 27 and 29 have reached their end of travel, ring 17 and collar 22 begin to couple connectors 12 and 13 together. When the "CIR" connector has locked itself together, the BAQCCV 10 is completely coupled and permits full unrestricted air flow through the two valve halves.

During uncoupling of the "CIR" connector, connectors 12 and 13 begin to separate, with the butterfly valve 36 in connector 12 being the first to begin its forward motion toward the seating surface at the end of inner valve housing 31, because of the greater pressure of compression spring 46 (last to open, first to close). As seen in FIG. 11B, as plunger 29 is pushed outward by compression spring 46, one edge of shaft portion 344 of the rotatable shaft 34 will engage with edge portion 42B of the enlarged end portion 42A of slots 42 as shaft 34 and butterfly valve 36 slide forward. Edge portion 42B is positioned in end portion 42A to cause shaft 34 to rotate in a direction (shown by the arrow in FIGS. 11B and 11C) opposite to the direction in which shaft 34 rotated as valve 36 was opening, thereby reloading the rotational torque on the biasing elements 44 as notches 343 reengage with slots 42 and the shaft moves forward to close valve 36. After the butterfly valve 36 has rotated 90 degrees to a position in which it is normal to the axis of inner valve housing 31, it seals the inside diameter of inner valve housing 31 as it slides toward the rest/closed position against flanges 40 at the end of inner valve housing 31 (see FIG. 6).

Once the valve 36 of connector 12 has closed, the compression spring 48 of connector 13 then forces plunger 27 in the forward direction in the same manner in which plunger 29 was moved, resulting in closure of valve 36 of supply side connector .13 in the same manner as that of receiving side connector 12, with both valves being completely sealed shut by the time the "CIR" connector has completely uncoupled.

Referring now to FIGS. 10A–I the operation of biasing elements 44 in rotating the shaft 34 will be further explained. A biasing element 44 may comprise an elastomeric bushing (FIGS. 10A–C) or a coil spring (FIGS. 10D–F). The elastomeric bushing fits snugly within pocket 292 and snugly around the outer circumference of square drive end 345 on rotatable shaft 34 such that the exterior surface of the bushing can not rotate in the pocket but the interior surface thereof engaging with square drive end 345 can rotate. As shown in FIG. 10C, when the valve is fully opened, the bushing is at rest. A 45 degree rotation of the shaft 34 in the clockwise direction causes the interior surface of the bushing to twist to the position shown in FIG. 10B while the exterior surface remains stationary. Rotation another 45 degrees to the position shown in FIG. 10A places the bushing under a full load rotational torque. When the shaft 34 reaches enlarged end portion 42A of slot 42 during valve coupling, this rotational torque causes the square drive end 345 to rotate a full 90 degrees in the opposite, i.e., counterclockwise, direction.

A coil spring used as the biasing element 44 operates to rotate the shaft in a similar manner as shown in FIG. 10D–F. As noted above, the respective spring ends are anchored to the plunger 29 via pocket 292 and to the square drive end 345 of shaft 34. It will be understood by those skilled in the art that a full rotational torque may be loaded on the biasing elements 44 (when the valve is in the closed position) by rotating the shaft 34 in a clockwise or counterclockwise direction ninety degrees from the rest, i.e. valve open, position.

Figure 10G:
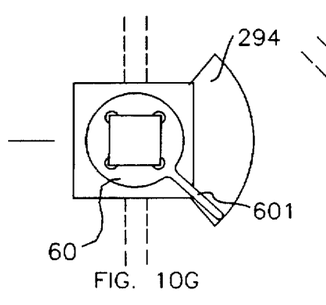
Figure 10H:
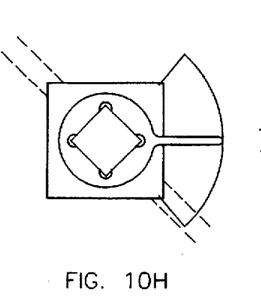
Figure 10I:
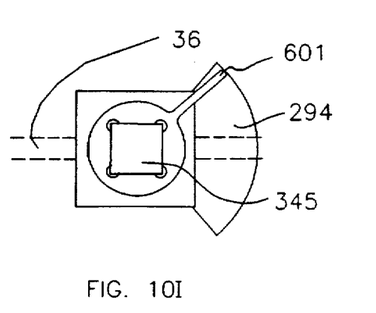

As shown in FIGS. 10G–I, the rotation of the shaft 34 may be limited to 90° by securing the biasing elements 44 onto the shaft ends 345 with a Tinnerman nut 60 having a timing arm 601 which rotates in a semicircular cutout 294 adjoining pocket 292 on plunger 29 (see FIGS. 9A and B). When the valve is closed as shown in FIG. 10G, the timing arm 601 abuts against a wall of the cutout 294. During rotation of the shaft 34, the Tinnerman nut 60 and timing arm 601 rotate within the pocket 292 and cutout 294, respectively, until the timing arm 601 abuts against the opposing wall of cutout 294, as shown in FIG. 10I. The semicircular cutout is arranged and adapted to limit the rotation of the timing arm, and thus the valve, to 90° from the valve closed position.

FIG. 11C shows an alternative embodiment wherein biasing elements 44 and Tinnerman/timing nut 60 may be eliminated. FIG. 11C shows groove 42 with end portion 42A as having a cam surface 421 which causes shaft 34 to rotate the valve between the closed position 11D and the open position 11E as the shaft reaches it furthermost travel.

Although presently preferred embodiments of the invention have been disclosed herein, it will be apparent to those of ordinary skill in the art that variations and modifications of the described embodiments may be made without departing from the spirit and scope of the invention. For example, the invention may be utilized as a valving mechanism for gases other than air, or more broadly, with fluids. Also, the "CIR" type connector could be replaced by various other connectors which are similar in function. For example, the connector need only be capable of causing the two plungers to push against each other while coupling the two connectors and forming a positive lock once the connectors are coupled. Accordingly, it is intended that the invention be limited only by the appended claims.

What is claimed is:

1. A quick coupling connector valve, comprising:
   (a) a first connector; and
   (b) a second connector for mating with said first connector, each of said first and second connectors comprising:
      (i) a valve housing having an interior surface defining a passageway having a longitudinal axis of symmetry;
      (ii) engagement means, mounted on said valve housing, for coupling and uncoupling the first and second connectors together;
      (iii) a plate-like valve member;
      (iv) means for supporting said plate-like valve member within said valve housing so as to be slidable axially between a first position and a second position along said axis of symmetry and rotatable about a radial axis orthogonal to said axis of symmetry, said radial axis being located at said second position intercepting said axis of symmetry, said plate-like valve member fitting against said interior surface of said valve housing to close said passageway when said plate-like valve member is oriented orthogonal to said axis of symmetry and said plate-like valve member opening said passageway when said plate-like valve member is oriented parallel to said axis of symmetry to allow fluid flow through said passageway;
      (v) means, responsive to operation of said engagement means to couple and uncouple the first and second connectors together, for sliding said plate-like valve member axially along said longitudinal axis of symmetry; and
      (vi) means for rotating said plate-like valve member at said second position about said radial axis which is orthogonal to said longitudinal axis of symmetry.

2. A connector valve according to claim 1, wherein:
   said valve housing has first and second longitudinal through-slots located at diametrically opposed positions relative to said longitudinal axis of symmetry and extending a distance corresponding to said first and second positions on said longitudinal axis of symmetry;
   said valve member is connected to a rotatable shaft having first and second ends respectively extending through said first and second through-slots, said rotatable shaft being slidable within said first and second through-slots between said first and second positions;
   said first and second longitudinal through-slots comprising means for preventing rotation of said rotatable shaft at all positions except said second position;
   said means for supporting comprising a plunger positioned around an outer surface of said valve housing and concentric with said valve housing, said plunger having first and second through-holes in which said first and second ends of said rotatable shaft are disposed;
   said means for sliding comprises a compression spring for applying a force against said plunger tending to slide said plunger, said rotatable shaft and said valve member in a direction parallel to said longitudinal axis of symmetry from said second position to said first position; and
   said means for rotating applies a rotational torque to said first and second ends of said rotatable shaft positioned in said first and second through-holes such that when said rotatable shaft is located at said first position, said rotational torque is maximum and when said rotatable shaft is located at said second position, said rotational torque rotates said rotatable shaft to cause said plate-like valve member to be oriented parallel to said axis of symmetry.

3. A connector valve according to claim 2, wherein said means for rotating comprises: one of an elastomeric bushing and a coil spring.

4. A connector valve according to claim 2, wherein said plunger has an end portion axially projecting away from said valve housing when said rotatable shaft is located at said first position, said end portion having an end surface for abutting against an opposing end surface of the plunger of the other one of the first and second connectors as the first and second connectors are being coupled together by said engagement means, whereby the plungers of both the first and second connectors push against each other and their respective said compression springs to cause the valves of both the first and second connectors to slide within the valve housing away from said first position.

5. A connector valve according to claim 2, wherein:
   said first and second longitudinal through-slots each have a rectangular portion and an enlarged end portion, said enlarged end portion being located at said second position; and
   said rotatable shaft has two opposing notches for slidably engaging the rectangular portions of the first and second longitudinal through-slots, said rectangular portions comprising said means for preventing rotation, said rotatable shaft being free to rotate only within the enlarged end portion.

6. A connector valve according to claim 5, wherein:
   the means for rotating the shaft causes the shaft to rotate during uncoupling of the first and second connectors in a direction opposite to the direction in which the rotatable shaft rotates during coupling of the first and second connectors;
   said means for rotating the shaft comprises:
      first and second biasing elements respectively disposed in the first and second through-holes in the plunger, the biasing elements being engaged with the first and second ends of the rotatable shaft, whereby rotation of the rotatable shaft in one direction within the enlarged end portions of the through-slots loads the first and second biasing elements with a rotational torque and rotation of the rotatable shaft in the other direction releases the rotational torque; and
      means for limiting rotation of the rotatable shaft to a range of 90°.

7. A connector valve according to claim 6, wherein said rotation limiting means comprises a nut with a timing arm disposed on at least one of the ends of the rotatable shaft, the nut and timing arm being rotatable within the through-hole and a cutout adjoining the through-hole, respectively, with the cutout having opposing walls to limit rotation of the rotatable shaft to a range of 90° when the timing arm moves from one of the walls to the other wall during coupling and uncoupling of the first and second connectors.

8. A connector valve according to claim 6, wherein said rotation limiting means comprises a cam surface located in the enlarged end portion of the first and second through-slots, said cam surface stopping the rotation of the shaft notch in the enlarged portion at 90° during coupling of the first and second connectors.

9. A connector valve according to claim 1, wherein:

said engagement means of one of said first and second connectors includes a captive, rotatable ring having a plurality of spaced lugs on the inner surface of said ring; and said engagement means of the other one of said first and second connectors includes a plurality of helical grooves equal in number to the number of said lugs, said grooves being arranged to engage and interact with the lugs such that when the lugs are engaged and the ring is rotated, the lugs ride within the helical grooves to fully couple or uncouple the first and second connectors depending on the direction of rotation of the ring.

10. A connector valve according to claim 9, wherein said engagement means of the other one of the first and second connectors further includes pin means for locking the lugs in position at the end of each of the associated helical grooves, said lugs and said pin means being releasable by exertion of pressure on the ring in the direction opposite that in which the lugs were fully engaged in the helical grooves.

11. A connector valve according to claim 9, wherein said engagement means of one of said first and second connectors further comprises an axially projecting ring, and said engagement means of the other one of said first and second connectors further comprises a groove arranged to receive the projecting ring whereby the first and second connectors are prevented from rotating during coupling and uncoupling.

12. A connector valve according to claim 11, wherein said groove includes an O-ring disposed on its interior surface for forming a liquid tight seal against the inside diameter and outside diameter of said projecting ring when the first and second connectors are coupled together.

13. A connector valve according to claim 2, wherein the compression spring in one of the first and second connectors is more resistant than the compression spring in the other of the first and second connectors, whereby the valve in said other connector opens first and closes last during coupling and uncoupling of the first and second connectors.

14. A connector valve according to claim 2, wherein the compression spring in one of the first and second connectors has the same resistance as the resistance of the compression spring in the other of the first and second connectors, whereby the valves in both of the first and second connectors open simultaneously during coupling and uncoupling of the first and second connectors.

15. A connector valve according to claim 3, wherein the rotatable shaft has a mounting surface for receiving and attaching the valve member.

16. A connector valve according to claim 15, wherein the mounting surface is a cutout portion of the rotatable shaft having a flat bottom, the depth of the cutout being the same as the cutout thickness of the valve member.

* * * * *